United States Patent [19]

Kanzaki et al.

[11] Patent Number: 5,796,475
[45] Date of Patent: Aug. 18, 1998

[54] SIGNAL PROCESS METHOD AND APPARATUS FOR DEFECT INSPECTION

[75] Inventors: Toyoki Kanzaki; Dainichiro Kinoshita, both of Miyanohigashi-machi, Japan

[73] Assignee: Horiba, Ltd., Kyoto, Japan

[21] Appl. No.: 798,068

[22] Filed: Feb. 12, 1997

[30] Foreign Application Priority Data

Feb. 13, 1996 [JP] Japan ................. 8-051024

[51] Int. Cl.[6] ................................ G01N 21/88
[52] U.S. Cl. .................. 356/237; 356/431; 250/559.45
[58] Field of Search ........................ 356/237, 431; 250/559.41, 559.45, 559.48, 559.49

[56] References Cited

U.S. PATENT DOCUMENTS

| | | | |
|---|---|---|---|
| 3,780,215 | 12/1973 | Shibata et al. | 178/504 |
| 4,081,841 | 3/1978 | Ochi et al. | 250/208.1 |
| 4,468,120 | 8/1984 | Tanimoto et al. | 250/599.41 |
| 4,559,603 | 12/1985 | Yoshikawa | 356/237 |
| 4,610,541 | 9/1986 | Tanimoto et al. | 356/237 |
| 4,735,323 | 4/1988 | Okada et al. | 356/237 |
| 4,781,115 | 11/1988 | Ueda et al. | 250/559.41 |
| 4,791,586 | 12/1988 | Meada et al. | 356/237 |
| 5,098,191 | 3/1992 | Noguchi et al. | 356/237 |
| 5,311,275 | 5/1994 | Taniguchi et al. | |
| 5,321,495 | 6/1994 | Hagiwara et al. | |
| 5,583,635 | 12/1996 | Miura et al. | 356/338 |
| 5,638,134 | 6/1997 | Kameyama et al. | 348/607 |

Primary Examiner—Georgia Y. Epps
Assistant Examiner—Zandra V. Smith
Attorney, Agent, or Firm—Price, Gess & Ubell

[57] ABSTRACT

A signal processing method and an improved defect detecting apparatus which scans a circuit substrate with a laser beam is provided to enable a distinction between a circuit pattern signal and a defect signal. A laser beam is scanned across the surface of a substrate with the reflected light picked up by a photodetector. The photodetector provides an output signal that can comprise both a pattern signal and a defect signal. This output signal is applied to a first signal processing line having a low-pass filter characteristic and a second signal processing line without a low-pass filter characteristic. The signals can be appropriately amplified and/or delayed and are finally submitted to a subtraction circuit so that the resulting output signal enables a ready determination of a defect apart from the existence of any pattern signal.

5 Claims, 7 Drawing Sheets

PRIOR ART

SIGNAL PROCESS METHOD AND APPARATUS FOR DEFECT INSPECTION

BACKGROUND OF THE INVENTION

1. Field of the Invention

This invention relates to a signal processing method in a defect inspecting apparatus with which it is possible to detect whether or not defects adhere to the surface of the subject of inspection, such as a reticle or masks to be used for printing A circuit pattern onto a semiconductor wafer or product wafers formed with circuit patterns or further a substrate for liquid crystal devices, and further to identify the size of the defect and the place of adhesion.

2. Description of Related Art

Various forms of apparatus for detecting particles on a substrate are known, such as shown in U.S. Pat. No. 5,311,275 and U.S. Pat. No. 5,321,495.

Figure 6:
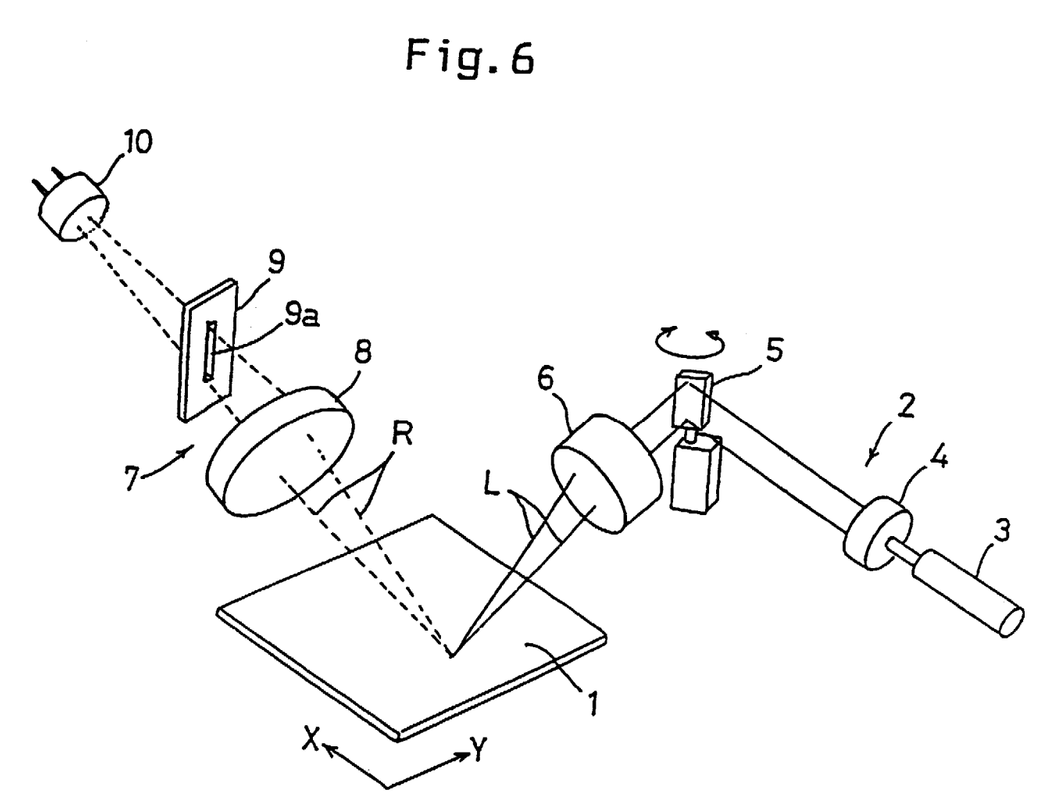
FIG. 6 is a schematic diagram to show schematically the general constitution of a defect inspection apparatus.

FIG. 6 shows a general constitution of a defect inspecting apparatus as mentioned above. In FIG. 6, the member 1 is a substrate on the surface of which a circuit pattern (not illustrated) is drawn, which is the subject of inspection (for example, a reticle), being placed horizontally on the not illustrated inspection stage. The inspection stage is made slidably movable in the arrow marked direction X in the drawing and the arrow marked direction Y which is orthogonally intersecting with the former and can also be adjusted in a vertical direction, if necessary.

The member 2 is in incident optical system for irradiating the laser beam L on the surface of the substrate of the inspection subject while scanning linearly in the arrow marked direction X. It comprises for example a He-Ne laser tube 3 for irradiating the laser beam L having a certain deflection angle, a beam expander 4, a galvano mirror 5, and a condenser lens 6, and the like, and is constituted so as to irradiate the laser beam L from the laser tube 3 from an obliquely upper direction of the substrate 1 of the inspection subject at a predetermined angle while linearly scanning in a reciprocal manner within a predetermined range in the direction X.

The member 7 is a detection optical system for detecting the scattered light R from the laser beam irradiation surface of the substrate 1 of the inspection subject, being disposed obliquely upward from one end side of the substrate 1 of the inspection subject in the direction X. This detection optical system 7 comprises a condenser lens 8, a slit member 9 formed with a narrow slit 9a for restricting the scattered light R and a photodetector 10 comprising for example a photomultiplier tube, and the like.

In the defect inspecting apparatus constituted as above, while moving linearly the inspection stage in an arrow marked direction Y, the laser beam L from the laser tube 3 is irradiated from the obliquely upward direction of the substrate 1 of the inspection subject at a predetermined angle while linearly scanning within the predetermined range in the direction X, and the scattered light R from the surface of the substrate 1 of the inspection subject is caused to be incident on the photodetector 10.

Figure 7:
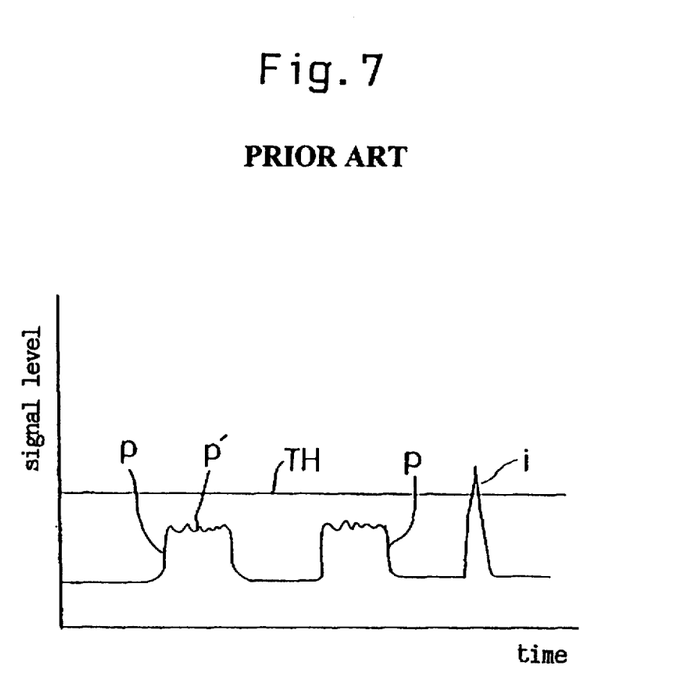
FIG. 7 is a schematic diagram to illustrate the prior art signal processing.

And, the output signal from the photodetector 10 includes, for example, as shown in FIG. 7, a signal (pattern signal) p obtainable on the basis of the scattered light from the pattern and the signal (defect signal) i obtained on the basis of the scattered light from the defect. While the pattern signal p has a trapezoidal shape with fine varying portions multilaid on the upper part, the defect signal i has a peak higher and acuter than the pattern signal p.

Conventionally, as shown in the mark TH in FIG. 7, a certain level threshold value is set, and it is identified to be the defect signal i when a signal exceeding said level is obtained, and it is identified to be the signal p based on the defect of a negligible degree or the pattern when the signal level is lower than the threshold value TH. Namely, it is so constituted that, by making comparison with the threshold value TH based on the detection result of the scattered light with the photodetector 10, inspection is made on the defect on the surface of the substrate 1 of the inspection subject.

By the way, according to the progress of the high LSI semiconductors in recent years, there have been required micronization and high density of circuit patterns, and the defects which should be detected have also become smaller. Because of this, the signal intensity from the pattern becomes stronger because of the increase in the patterns per unit area, but the signal strength from the defect to be detected becomes weaker. As a result, the threshold value TH as shown in FIG. 7 is lowered, and the pattern signal p may exceed the threshold value TH, thereby causing a risk of showing a false detection.

There is a need in the prior art to address these problems of micronization in an effective and economical manner.

OBJECTS AND SUMMARY OF THE INVENTION

This invention has been made with particular attention paid to the matters stated above, and its object is to provide a signal processing method (hereinafter to be referred to simply as signal processing method) in an improved defect detecting apparatus with which it is possible to make an exact identification between the pattern signal and the defect or a foreign signal, and to accurately detect the existence and location of defects on the inspection subject.

In order to attain the above object, the signal processing method of this invention comprises mutually parallel arrangements of a first signal processing line provided with a low-pass filter characteristic and a second signal processing line not provided with a low-pass characteristic on the output side of the photodetector, so as to take the difference of the outputs of these two signal processing lines.

Figure 1:
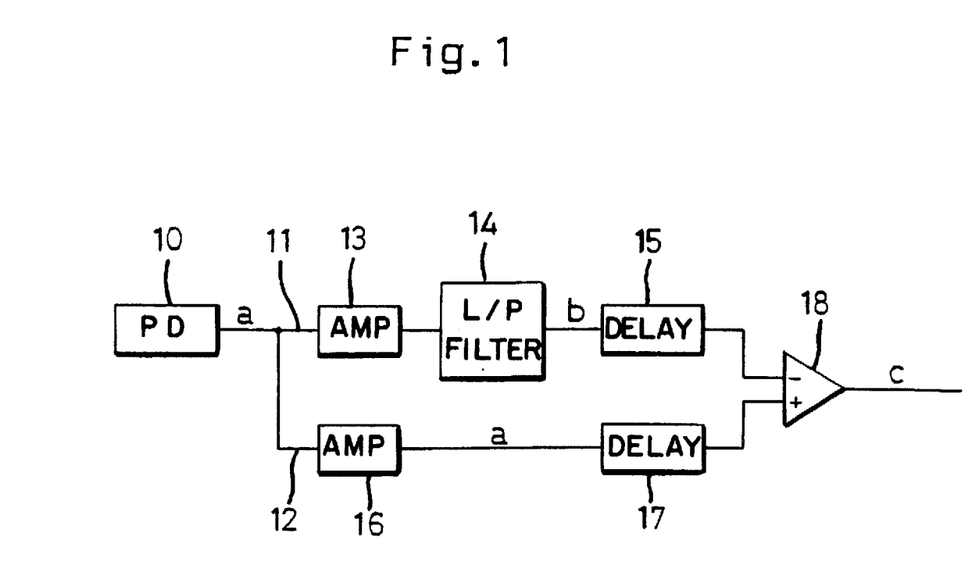
FIG. 1 is a schematic diagram to show the first embodiment of the invention.

To explain the operations of the signal processing method having the above constitution with reference to FIG. 1, the output a from the photodetector 10 is inputted respectively to the two signal processing lines 11, 12 which are mutually parallel to each other.

Figure 4A:
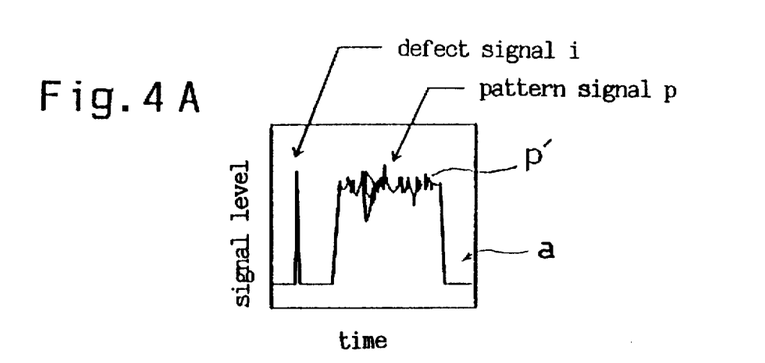

The signal a inputted to the first signal processing line 11 becomes a signal b by going through the low-pass filter 14 which does not pass the defect signal or the upper part of the pattern signal showing rapid change [e.g. the part shown in the mark p' in FIG. 4(A)], and is inputted to the subtraction circuit 18.

The signal a inputted to the second signal processing line 12 passes through the rapidly responding amplifier 16 in a manner not to distort the shape as far as possible, and is inputted to the above subtraction circuit 18 through the appropriate delay circuit 17. In the subtraction circuit 18, by taking the difference between the signal b of the first signal processing line 11 and the signal a of the second signal processing line 12, a signal which can clearly distinguish the defect signal from the pattern signal is obtained.

Figure 2:
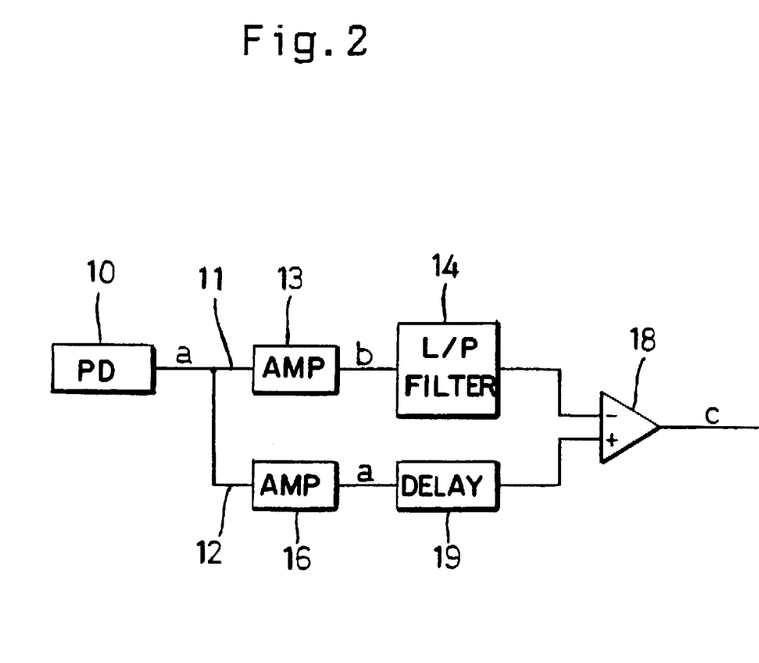
FIG. 2 is a schematic diagram to show the second embodiment of the invention.

In taking the difference as above, it is necessary to arrange the signals b and a in the first signal processing line 11 and the second signal processing line 12 to be simultaneously inputted to the subtraction circuit 18. This is settled by either providing adequate delay circuits 15 and 17 on the two signal processing lines 11 and 12 or providing a delay circuit 19 only on the second signal processing line 11 not having a low-pass filter characteristic (ref. FIG. 2).

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 4(A)–FIG. 4(C) are the schematic diagrams to illustrate the operation in the case where the defect signal and the pattern signal are not overlapped;

FIG. 5(A)–FIG. 5(C) are the schematic diagrams to illustrate the operation in the case where the defect signal and the pattern signal are overlapped;

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a signal processing method in an improved defect inspecting apparatus. Hereinafter, the preferred embodiments of this invention are illustrated with reference to the drawings.

FIG. 1 schematically shows a circuit constitution for realizing the signal processing method of this invention. This signal processing circuit is provided on the output side of the photodetector 10 in the defect inspection apparatus shown in FIG. 6.

In FIG. 1, the members 11 and 12 are the mutually parallel signal processing lines provided on the output side of the photodetector 10. A signal processing line on one side (hereinafter to be referred to as the first signal processing line) 11 is constituted to have a low-pass filter characteristic, and the signal processing line on the other side (hereinafter to be referred to as the second signal processing line) 12 is not furnished with a low-pass filter characteristic.

The first signal processing line 11 is provided with an amplifier 13, a low-pass filter 14, and a delay circuit 15, in series one after another. The amplifier 13 appropriately amplifies the output a from the photodetector 10 without modifying its configuration. The low-pass filter 14 is so designed as not to pass the foreign signal i or rapidly varying component p' at the upper part of the pattern signal p as shown for example in FIG. 4(A) but to pass only the original pattern signal p. And, the characteristics of this low-pass filter 14 are determined on the basis of the scan velocity of the laser beam L on the substrate 1 in FIG. 6, the beam diameter thereof, the shape and size of the subjective pattern, the size of the defect to be detected, the intensity of the scattering light R and the like. The delay circuit 15 is to output the output b of the low-pass filter 14 by delaying a predetermined time.

The second signal processing line 12 is provided with an amplifier 16 and a delay circuit 17 in series with each other. The amplifier 16 is to amplify appropriately the output a from the photodetector 10 without modifying its shape, and its amplitude is set to be equal to that of the amplifier 13 provided on the first signal processing line 11. The delay circuit 17 is to output the output a of the amplifier 16 by delaying by a predetermined length of time. Its delay time is set to be larger than that of the delay circuit 15 provided in the first signal processing line 11, so that the output b of the first signal processing line 11 and the output a of the second signal processing line 12 are inputted simultaneously to the later described subtraction circuit 18.

The member 18 is a subtraction circuit for taking a difference between the output b of the first signal processing line 11 and the output a of the second signal processing line 12, and c is the output of it.

The operation of the signal processing circuit having the above constitution is explained with reference to FIG. 4 as well. Now, in a defect inspecting apparatus shown in FIG. 6, while moving linearly the inspection stage in the arrow marked direction Y, the laser beam L from the laser tube 3 is irradiated from the obliquely upward direction of the substrate 1 of the inspection subject at a predetermined angle while linearly scanning within the predetermined range in the direction X, and the scattered light R from the surface of the substrate 1 of the then inspection subject is caused to be incident on the photodetector 10. And, it is assumed that an output signal a as shown for example in FIG. 4(A) is outputted from the photodetector 10.

Figure 4B:
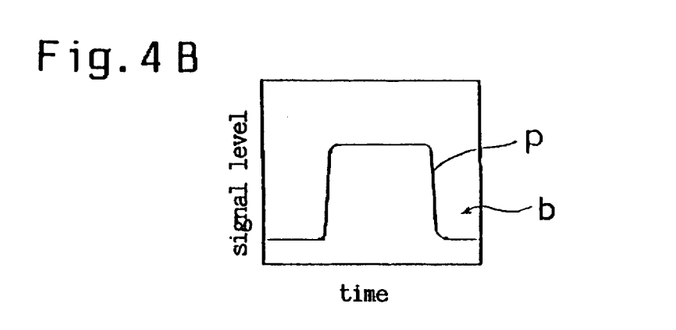

The above signal a includes, for example, as shown in FIG. 4(A), a defect signal i and a pattern signal p at a moderate time difference. However, their levels are nearly equal, and the two signals are not clearly distinguishable. The signal a outputted from the above photodetector 10 is inputted to the first signal processing line 11 and the second signal processing line 12, respectively. The signal a inputted to the first signal processing line 11 is appropriately amplified with the amplifier 13, after which it is inputted to the low-pass filter 14. In the low-pass filter 14, the defect signal i and the rapidly varying component p' at the upper part of the pattern signal p are cut, and the signal b as shown in FIG. 4(B) is outputted from the low-pass filter 14. This signal b is delayed by a predetermined length of time in the delay circuit 15, after which it is inputted to one terminal of the subtraction circuit 18.

The signal a inputted to the second signal processing line 12 is appropriately amplified with the amplifier 16, after which it is inputted to the delay circuit 17. And, this signal a is delayed by a predetermined length of time in the delay circuit 17, after which it is inputted to the other terminal of the subtraction circuit 18.

Figure 4C:
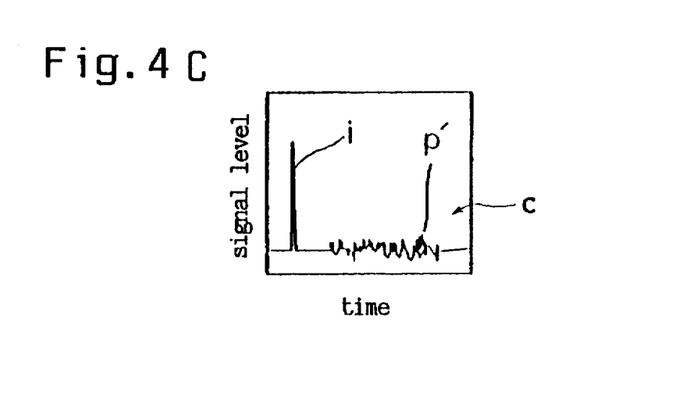

In the subtraction circuit 18, the output b of the first signal processing line 11 and the output a of the second signal processing line 12 are simultaneously inputted, wherein an operation of a–b is carried out, by which a signal c as shown in FIG. 4(C) is outputted from the subtraction circuit 18. In this signal c, the defect signal i and the other signal p' can be clearly distinguished.

Figure 5A:
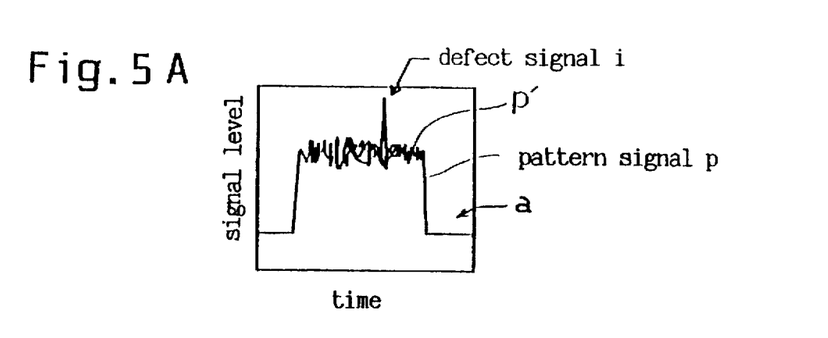
Figure 5B:
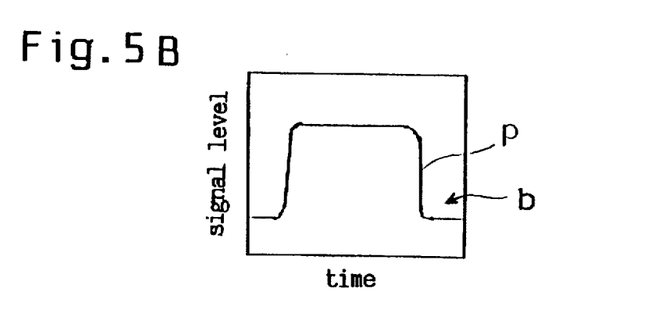
Figure 5C:
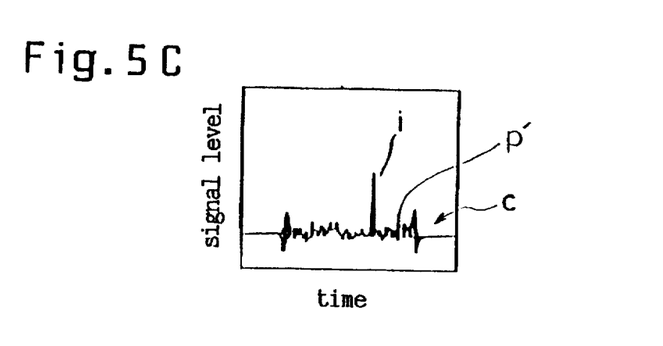

By the way, the foregoing embodiment referred to the case where the signal a as shown in FIG. 4(A) is outputted from the photodetector 10, which is the case where the defects are present at a position other than the pattern forming position. However, when the defect is present at the pattern forming position, a signal a as shown in FIG. 5(A) is outputted from the photodetector 10. In this case also, by treating in the same manner as described above, a signal c as shown in FIG. 5(C) is obtainable.

This invention is not limited to the first embodiment as stated above but may be practiced in various modifications. For example, in the first embodiment, the setting positions of the low-pass filter 14 and the delay circuit 15 may be inverted, and, as shown in FIG. 2, the delay circuit 19 may be provided only in the second signal processing line 12. According to this second embodiment, the constitution is more simplified than in the first embodiment.

Though illustration is omitted, it may be so set that, in the first embodiment and the second embodiment above, an amplifier is provided on the output side of the photodetector 10, and the output of this amplifier is supplied to the first signal processing line 11 and the second signal processing line 12. By this arrangement, the number of the amplifiers can be reduced, and the constitution can be more simplified.

Figure 3:
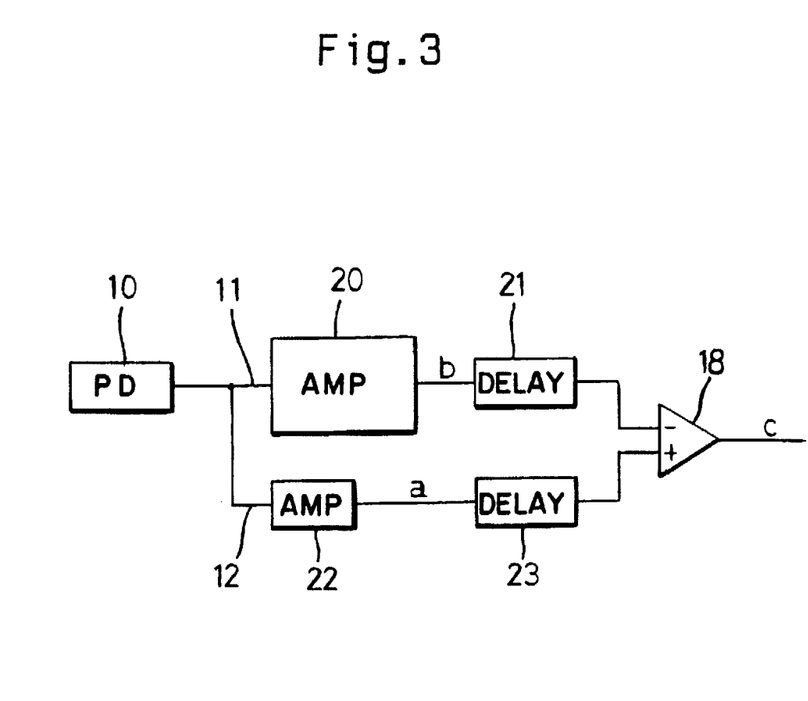
FIG. 3 is a schematic diagram to show the third embodiment of the invention/

In each of the above embodiments, a low-pass filter 14 is provided on the first signal processing line 11 side so that the first signal processing line 11 has a low-pass characteristic. However, instead of this arrangement, constitution may be made as shown in FIG. 3. Namely, FIG. 3 shows the third embodiment of this invention, wherein the first signal processing line 11 is provided with an amplifier 20 having a large response time constant and a delay circuit 21 at the rear stage of the former, and on the other hand, the second signal processing line 12 is provided with an amplifier 22 and a delay circuit 23. The amplifier 22 has the same function as the amplifiers 13 and 16 in the first embodiment. Further, the relations between the delay circuit 21 and the delay circuit 23 are the same as those between the delay circuit 15 and the delay circuit 17 in the first embodiment. It does without saying that the third embodiment constituted as above shows the same functions as the first embodiment, and, needless to say, in this embodiment, the delay circuit 21 may be omitted, and only the second signal processing line 12 may be provided with an appropriate delay circuit.

Further, in all the foregoing embodiments, a single photodetector 10 is used. Needless to say, however, the same application can be made with the defect inspecting apparatus provided with a plurality of detectors.

This invention is practiced in the embodiments as described above, and shows the following effects. According to the signal processing method of this invention, in case a defect signal is contained in the output from the photodetector, such signal can be selectively left over, so that it is possible to identify the defect signal more definitely than with the prior art system. Accordingly, the defect on the inspection subject and the pattern can be clearly and strictly distinguished and the detection of the defect can be exactly performed.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A signal processing method for a defect inspecting apparatus in which a laser beam is irradiated on the surface of the inspection subject while scanning, and the scattered light from the surface of the inspection subject is caused to be incident on the photodetector, so that the foreign matter can be inspected on the basis of the detection result of the scattered light with the photodetector outputting a detection signal, comprising the steps of:

dividing the detection signal into parallel arrangements of a first signal processing path with a low-pass filter characteristic and a second signal processing path without a low-pass filter characteristic; and comparing an output of the first signal processing path with an output of the second processing path to determine the existence of foreign matter.

2. A signal processing method for a defect inspecting apparatus as set forth in claim 1, further providing a delay circuit only on the second signal processing path before comparing the outputs.

3. A particle detecting apparatus for detecting particles on an object comprising:

means for scanning an object with a light beam along scan lines;

detecting means for detecting light from the object which has been incident from the scanned light beam to provide a detection signal;

means for processing the detection signal including dividing the detector signal into a first and second signal;

means for amplifying the first and second signals;

means for filtering the first signal with a low-pass filter to provide a filtered first signal;

means for delaying the second signal; and means for comparing the filtered first signal with the delayed second signal to determine the existence of particles.

4. A particle detecting apparatus for detecting particles on an object comprising:

means for scanning an object with a light beam along scan lines;

detecting means for detecting light from the object which has been incident from the scanned light beam to provide a detection signal;

means for processing the detection signal including dividing the detector signal into a first and second signal;

means for amplifying the first and second signals;

means for delaying the first and second signal; and means for comparing the first signal with the second signal to determine the existence of particles.

5. A particle detecting apparatus for detecting particles on an object comprising:

means for scanning an object with a light beam along scan lines;

detecting means for detecting light from the object which has been incident from the scanned light beam to provide a detection signal;

means for processing the detection signal including dividing the detector signal into a first and second signal;

means for amplifying the first and second signals;

means for filtering the first signal with a low-pass filter to provide a filtered first signal;

means for delaying the first and second signals; and
means for comparing the delayed filtered first signal with the delayed second signal to determine the existence of particles.

* * * * *